United States Patent [19]

Walton

[11] Patent Number: 5,543,153
[45] Date of Patent: Aug. 6, 1996

[54] ANTACID

[75] Inventor: William C. Walton, Fulwell, England

[73] Assignee: Sterling Winthrop Inc., Pittsburgh, Pa.

[21] Appl. No.: 204,574

[22] Filed: Mar. 1, 1994

Related U.S. Application Data

[63] Continuation of Ser. No. 936,688, Aug. 27, 1992, Pat. No. 5,330,760.

[51] Int. Cl.$^6$ ............................................. A61K 9/20
[52] U.S. Cl. .................... 424/466; 424/464; 424/465; 424/489; 424/441; 514/819
[58] Field of Search .................... 424/466, 464, 424/465, 489, 441; 514/819

[56] References Cited

U.S. PATENT DOCUMENTS

| | | | |
|---|---|---|---|
| 5,178,878 | 1/1993 | Wehling et al. | 424/466 |
| 5,223,264 | 6/1993 | Wehling et al. | 424/466 |
| 5,225,197 | 7/1993 | Bolt et al. | 424/466 |

FOREIGN PATENT DOCUMENTS 60237947  4/1986  Japan.

*Primary Examiner*—James M. Spear
*Attorney, Agent, or Firm*—Frederik W. Stonner

[57] ABSTRACT

A solid effervescent antacid formulation comprising as primary ingredients from about 35 to about 53 percent by weight of calcium carbonate, from about 0 to about 14 percent by weight of magnesium carbonate, from about 3.5 to about 7 percent by weight of a bicarbonate salt, from about 3.5 to about 7 percent by weight of malic acid and from about 21 to about 35 percent by weight of a bulking agent.

6 Claims, No Drawings

ANTACID

This application is a continuation of application Ser. No. 07/936,688, filed Aug. 27, 1992, U.S. Pat. No. 5,330,760.

BACKGROUND OF THE INVENTION

1. Field of the Invention

The invention relates to an antacid formulation and more specifically to a solid effervescent antacid formulation comprising calcium carbonate, optionally in combination with magnesium carbonate, as the antacid component, a combination of a bicarbonate salt and malic acid as the effervescent component, and a bulking agent.

2. Information Disclosure Statement

The use of calcium carbonate as an antacid either alone or in combination with other antacids such as magnesium carbonate and magnesium hydroxide is known.

The use of sodium bicarbonate in effervescent salts and of citric acid as an acidulant in effervescent salts, powders and tablets is known as is the use of sodium bicarbonate and citric acid in combination in antacid formulations. One such antacid formulation marketed as a tablet to be dissolved in water to produce an effervescent antacid solution contains sodium and potassium bicarbonate and citric acid.

Antacid formulations have been marketed in various forms such as chewing gums, tablets, lozenges, powders and liquids. Many antacid formulations intended to be taken in solid form tend to leave a rather unpleasant chalky taste in the mouth. This problem is overcome by the present invention.

SUMMARY OF THE INVENTION

This invention is the result of a project whose goal was the development of an antacid formulation to be taken in solid form which, on exposure to saliva, would effervesce gently thereby providing a good mouth feel characterized by a pleasant fizzing and tingling sensation on the tongue and a pleasant non-chalky aftertaste. In the course of developing a suitable antacid formulation having the sought after characteristics, an antacid formulation was prepared comprising a combination of calcium and magnesium carbonates as the antacid component and a combination of sodium bicarbonate and citric acid as the effervescent component. However, the desired fizz/tingle sensation and mouth feel was not realized using citric acid. Surprisingly it was found that the substitution of malic acid for the citric acid in equivalent amount resulted in an antacid formulation having the desired characteristics of causing a pleasant fizz/tingle sensation on the tongue and leaving a pleasant non-chalky aftertaste.

Thus the invention provides, in one aspect, a solid effervescent antacid formulation comprising, as the primary ingredients, from about 35 to about 53 percent by weight of the primary ingredients of calcium carbonate and from about 0 to about 14 percent by weight of the primary ingredients of magnesium carbonate as the antacid component; from about 3.5 to about 7 percent by weight of the primary ingredients of a bicarbonate salt and from about 3.5 to about 7 percent by weight of the primary ingredients of malic acid as the effervescent component; and from about 21 to about 53 percent by weight of the primary ingredients of a bulking agent.

In a further aspect the invention provides the solid effervescent antacid formulation defined above in chewable tablet form.

DETAILED DESCRIPTION INCLUSIVE OF PREFERRED EMBODIMENTS

The primary ingredients in the solid effervescent antacid formulation are calcium carbonate, optionally in combination with magnesium carbonate, a bicarbonate salt, malic acid and a bulking agent.

Calcium carbonate or a combination of calcium and magnesium carbonates constitutes the antacid component of the solid effervescent antacid formulation. Calculated on the weight of the primary ingredients, the amount of calcium carbonate should be from about 35 to about 53 weight percent, preferably from about 38 to about 46 weight percent and of magnesium carbonate from about 0 to about 14 weight percent. When magnesium carbonate is employed, the amount thereof preferably is from about 4 to about 14 percent by weight of the primary ingredients, more preferably from about 4 to about 12 weight percent.

A combination of a bicarbonate salt and malic acid constitute the effervescent component of the solid effervescent antacid formulation. Calculated on the weight of the primary ingredients, the amount of the bicarbonate salt should be from about 3.5 to about 7.0 weight percent, preferably from about 4.8 to about 5.9 weight percent and of malic acid should be from about 3.5 to about 7.0 weight percent, preferably from about 4.8 to about 5.9 weight percent. The bicarbonate salt is selected from potassium and sodium bicarbonates, the latter being preferred. A mixture of such salts also may be employed.

The bulking agent should be pharmaceutically acceptable and, in addition to providing appropriate bulk to the solid effervescent antacid formulation, have properties which will contribute to the palatability of the formulation. When the antacid formulation is to be formulated as a tablet, the bulking agent should also have good compression characteristics. Suitable bulking agents are well known in the pharmaceutical formulating art. Preferably the bulking agent is a sweetener such as sugars, e.g., sucrose; and polyhydric alcohols, e.g., mannitol, sorbitol and xylitol, and mixtures thereof. A preferred bulking agent is sucrose. The bulking agent is employed in an amount of from about 21 to about 53 percent by weight, preferably from about 34 to about 41 percent by weight of the primary ingredients.

The solid effervescent antacid formulation may have incorporated therein effective amounts of optional pharmaceutically acceptable ingredients in order to impart thereto additional desirable properties, such as, but not limited to, sweetening agents, flavorants and colorants. The selection of such optional ingredients and amounts thereof to be employed is well within the skill of the art. Examples of sweetening agents which may be used are saccharin and salts thereof, cyclamic acid and salts thereof, acesulfame and salts thereof, and aspartame.

It is preferable, in order to avoid a gritty taste, to sieve the ingredients of the solid effervescent antacid formulation to a primary particle size not exceeding about 900 microns.

The solid effervescent antacid formulation is intended to be administered as a solid and may be formulated for use as a powder, granules or tablet, the latter being preferred. When formulated as a tablet, it is preferable to incorporate in the antacid formulation one or more tablet lubricating agents such as are well known in the art, e.g., stearic acid, magnesium stearate and talc. The amount of the tablet lubricating agent(s) required in the antacid formulation can be readily determined by the skilled formulator. Generally the amount will be from about 3.5 to about 4.5 weight percent calculated on the weight of the antacid tablet.

The solid effervescent antacid formulation can be formulated for use by granulation, blending and tableting techniques which are well known and conventional in the art.

The invention is illustrated by, but not limited to, the following example.

An antacid tablet of the invention was prepared having the following composition:

| Ingredient | Weight-Percent | Mg/Tablet | Funtion |
| --- | --- | --- | --- |
| Calcium carbonate | 40.24 | 600.0 | antacid |
| Magnesium carbonate | 8.38 | 125.0 | antacid |
| Sodium bicarbonate | 5.37 | 80.0 | $CO_2$ source |
| Malic acid | 5.37 | 80.0 | acidulant/taste |
| Sucrose | 36.12 | 538.5 | bulking agent |
| Saccharin sodium | 0.13 | 2.0 | sweetener |
| Magnesium stearate | 0.50 | 7.5 | tablet lubricant |
| Talc | 3.35 | 50.0 | tablet lubricant |
| Orange flavor | 0.54 | 8.0 | flavor |
| Total: | 100.00 | 1491.0 | |

The above tablet was prepared from a granulation prepared by a dry-blend method in which typical batch sizes were 1000K. All ingredients were sieved through a 20 mesh (900 micron) stainless steel sieve into a stainless steel bulk container. The low weight ingredients were diluted with sucrose prior to sieving. The particle size of the calcium and magnesium carbonates was less than 75 microns. The bulk material was transferred to a blending machine and tumbled until a uniform granulation was obtained (about 20 minutes). The granulation was then compressed into tablets on a high speed rotary tablet compression machine.

The above exemplified antacid tablet, when chewed, readily disintegrated while imparting a pleasant fizzing and tingling sensation to the tongue and left a pleasant non-chalky, non-gritty aftertaste.

What is claimed is:

1. A solid effervescent antacid formulation comprising, as the primary ingredients, from about 35 to about 53 percent by weight of the primary ingredients of calcium carbonate and from about 0 to about 14 percent by weight of the primary ingredients of magnesium carbonate as the antacid component; from about 3.5 to about 7 percent by weight of the primary ingredients of a bicarbonate salt and from about 3.5 to about 7 percent by weight of the primary ingredients of malic acid as the effervescent component; and from about 21 to about 53 percent by weight of the primary ingredients of a bulking agent.

2. A solid effervescent antacid formulation comprising, as the primary ingredients, from about 35 to about 53 percent by weight of the primary ingredients of calcium carbonate and from about 4 to about 14 percent by weight of the primary ingredients of magnesium carbonate as the antacid component; from about 3.5 to about 7 percent by weight of the primary ingredients of a bicarbonate salt and from about 3.5 to about 7 percent by weight of the primary ingredients of malic acid as the effervescent component; and from about 21 to about 53 percent by weight of the primary ingredients of a bulking agent.

3. An antacid formulation according to claim 2 which, calculated on the weight of the primary ingredients, comprises from about 38 to about 46 percent by weight of calcium carbonate, from about 4 to about 12 percent by weight of magnesium carbonate, from about 4.8 to about 5.9 percent by weight of the bicarbonate salt, from about 4.8 to about 5.9 percent by weight of malic acid and from about 34 to about 41 percent by weight of the bulking agent.

4. An antacid formulation according to claim 3 which, calculated on the weight of the primary ingredients, comprises about 42.15 percent by weight of calcium carbonate, about 8.78 percent by weight of magnesium carbonate, about 5.62 percent by weight of sodium bicarbonate, about 5.62 percent by weight of malic acid, and the remainder to 100 percent by weight of sucrose.

5. An antacid formulation according to claim 4 which additionally includes a sweetening agent.

6. An antacid formulation according to claim 3 in tablet form.

* * * * *